(12) United States Patent
Bissery

(10) Patent No.: US 6,545,010 B2
(45) Date of Patent: Apr. 8, 2003

(54) COMPOSITION COMPRISING CAMPTOTHECIN OR A CAMPTOTHECIN DERIVATIVE AND A PLATIN DERIVATIVE FOR THE TREATMENT OF CANCER

(75) Inventor: Marie-Christine Bissery, Vitry sur Seine (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/799,663

(22) Filed: Mar. 7, 2001

(65) Prior Publication Data

US 2001/0041712 A1 Nov. 15, 2001

Related U.S. Application Data

(60) Provisional application No. 60/193,398, filed on Mar. 31, 2000, and provisional application No. 60/190,055, filed on Mar. 17, 2000.

(51) Int. Cl.$^7$ .................. A61K 31/44; A61K 31/28; A61K 33/24
(52) U.S. Cl. .................. 514/283; 514/492; 424/649
(58) Field of Search .................. 514/283, 492; 424/649

(56) References Cited

U.S. PATENT DOCUMENTS

| 4,473,692 A | 9/1984 | Miyasaka et al. |
| 4,545,880 A | 10/1985 | Miyasaka et al. |
| 6,191,119 B1 | 2/2001 | Rubinfeld |

FOREIGN PATENT DOCUMENTS

| EP | 0 056 692 B1 | 7/1982 | |
| EP | 0 074256 B1 | 3/1983 | |
| EP | 0 088 642 A2 | 9/1983 | |
| EP | 0 296 612 B1 | 12/1988 | |
| EP | 0 321 122 B1 | 6/1989 | |
| EP | 0 325 247 B1 | 7/1989 | |
| EP | 0 540 099 B1 | 5/1993 | |
| EP | 0 715 854 A2 * | 6/1996 | .................. 514/492 |
| EP | 0 737 686 B1 | 10/1996 | |
| WO | WO 90/03169 | 4/1990 | |
| WO | WO 96/37496 | 11/1996 | |
| WO | WO 96/38146 | 12/1996 | |
| WO | WO 96/38449 | 12/1996 | |

OTHER PUBLICATIONS

Boku et al., J.clin Oncol. (1999), 79(5/6), 984–990 ABSTRACT ONLY.*
Sugiyama et al., Cancer Lett. (Shannon, Irel.) (1998), 128(2), 211–218 ABSTRACT ONLY.*
Kobayashi et al., Cancer Chemother. Pharmcol. (1998), 42(1), 53–58 ABSTRACT ONLY.*
Mirabelli, C.K., et al., "A Murine Model to Evaluate the Ability of in Vitro Clonogenic Assys to Predict the Response to Tumors in Vivo", *Cancer Research, Official Journal of the American Association for Cancer Research*, vol. 48, No. 19, pp. 5447–5454, Oct. 1, 1988.

T.H. Corbett et al., "Evaluation of Single Agents and Combinations of Chemotherapeutic Agents in Mouse Colon Carcinomas," *Cancer*, 40(5):2660–2680 (1977).

T.H. Corbett et al., "Response of Transplantable Tumors of Mice to Anthracenedione Derivatives Alone and in Combination with Clinically Useful Agents," *Cancer Treatment Reports*, 66(5):1187–1200 (May 1982).

David L. Emerson et al., "In vivo Antitumor Activity of Two New Seven–substituted Water–soluble Camptothecin Analogues," *Cancer Research*, 55:603–609 (Feb. 1995).

Isabelle Madelaine et al., "Sequential Modifications of Topoisomerase I Activity in a Camptothecin–Resistant Cell Line Established by Progressive Adaptation," *Biochemical Pharmacology*, 45(2):339–348 (1993).

Tomio Furuta and Teruo Yokokura, "Combination Therapy of CPT–11, a Camptothecin Derivative, with Various Antitumor Drugs Against L1210 Leukemia," *Japanese Journal of Cancer and Chemotherapy*, 18(3):393–402 (Mar. 1991); English Abstract p. 402.

Abstract: Japio No. 00965715 for JP 57–116015.
Abstract: Japio No. 00965774 for JP 57–116074.
Abstract: Japio No. 01293588 for JP 59–5188.
Abstract: Japio No. 01541290 for JP 60–19790.
Abstract: Japio No. 02948687 for JP 1–246287.
Abstract: Japio No. 02952177 for JP 1–249777.
Abstract: Derwent No. 01984–110813/198418 for JP 59–051289.

Masahiro Fukuoka and Noriyuki Masuda, "Clinical Studies of Irinotecan Alone and in Combination with Cisplatin," *Cancer Chemotherap. Pharmacology*, 34(Suppl):S105–S111 (1994).

Kensei Tobinai et al., "Combination Phase I/II Study of Irinotecan Hydrochloride (CPT–11) and Carboplatin in Relapsed or Refractory Non–Hodgkin's Lymphoma," *Jpn. J. Clin. Oncol.*, 26(6):455–460 (1996).

A. Yokoyama et al., "Phase I/II Study of Irinotecan (CPT–11) and Cisplatin (P) Plus Concurrent Thoracic Radiation Therapy (TRT) in Stage III Non–Small Cell Lung Cancer (NSCLC: A Japan Clinical Oncology Group (JCOG) Trial," *Proc. Am. Soc. Clin. Oncol.*, 15(–):407 AB:1242 (1996).

* cited by examiner

Primary Examiner—Jerome D. Goldberg
(74) *Attorney, Agent, or Firm*—Finnegan, Henderson, Farabow, Garrett & Dunner LLP

(57) ABSTRACT

The present invention relates to therapeutic associations for the treatment of cancer, comprising an effective amount of a camptothecin, or a camptothecin derivative, with an effective amount of an alkylating agent such as a platin derivative, and methods of using such therapeutic associations.

16 Claims, 2 Drawing Sheets

EVALUATION OF CPT-11 IN COMBINATION WITH CISPLATIN AGAINST
COLON ADENOCARCINOMA C51 ON BALB/C FEMALE MICE

BCM-915 (02.06.97-06.06.97)

| AGENT (BATCH) | ROUTE | DOSAGE IN MG/KG/DOSE | SCHEDULE IN DAYS | TOTAL DOSE IN MG/KG | FRACTION OF HNTD | DRUG DEATH (DAYS OF DEATH) | AVERAGE BODY WEIGHT CHANGE IN % PER MOUSE AT NADIR (DAY OF NADIR) |
|---|---|---|---|---|---|---|---|
| CPT-11 | P.O. 0.2 ml | 132.2 | 4 TO 7 (2x/D) | 1057.6 | | 5/5 (10, 3D13, 14) | -34.0 (12) |
| | | 82.2 | | 656.0 | | 0/5 | -22.4 (9) |
| | | 50.8 | | 406.4 | 1 | 0/5 | -12.3 (9) |
| | | 31.5 | | 252.0 | | 0/5 | -6.7 (7) |
| CISPLATIN | I.V. 0.2 ml | 8.0 | 4, 7 | 16.0 | | 5/5 (2D6, 10, 2D11) | - |
| | | 5.0 | | 10.0 | | 2/5 (13, 30) | -30.9 (12) |
| | | 3.1 | | 6.2 | 1 | 0/5 | -14.1 (10) |
| | | 1.9 | | 3.8 | | 0/5 | -5.2 (9) |
| CPT-11 CISPLATIN | P.O. 0.2 ml I.V. 0.2 ML | 61.5 3.75 | 4 TO 7 (2x/D) 4, 7 | 492.0 7.5 | 1.20) 2.40 1.20) | 1/5 (13) | -35.3 (12) |
| | | 49.2 3.0 | | 393.6 6.0 | 0.97) 1.94 0.97) | 0/5 | 28.0 (12) |
| | | 36.9 2.25 | | 295.2 4.5 | 0.73) 1.46 0.73) | 0/5 | -14.7 (9) |
| | | 24.6 3.0 | | 196.8 6.0 | 0.48) 1.45 0.97) | 0/5 | -27.6 (12) |
| | | 49.2 1.5 | | 393.6 3.0 | 0.97) 1.45 0.48) | 0/5 | -17.6 (10) |
| | | 24.6 1.5 | | 196.8 3.0 | 0.48) 0.98 0.48) | 0/5 | -14.3 (9) |
| | | 12.3 0.75 | | 98.4 1.5 | 0.24) 0.48 0.24) | 0/5 | -5.4 (8) |
| CONTROL | | | | | | | |

TUMOR DOUBLING TIME = 2.6 DAYS. MICE AVERAGE WEIGHT: CPT-11 = 22.51 g, CISPLATIN = 24.26 g, COMBINATION = 23.30 g. ABBREVIATIONS USED: BWL = BODY WEIGHT LOSS, HNTD = HIGHEST NONTOXIC DOSE.

*FIG. 1a*

EVALUATION OF CPT-11 IN COMBINATION WITH CISPLATIN AGAINST COLON ADENOCARCINOMA C51 ON BALB/C FEMALE MICE

| AGENT (BATCH) | MEDIAN TUMOR WEIGHT IN MG ON DAY 20 (RANGE) | T/C IN % DAY 20 | TIME FOR MEDIAN TUMOR TO REACH 1000 mg IN DAYS | T-C IN DAYS | LOG CELL KILL TOTAL | TUMOR FREE SURVIVORS DAY 120 | COMMENTS |
|---|---|---|---|---|---|---|---|
| CPT-11 | - | - | - | - | - | 0/5 | TOXIC |
|  | - | - | - | - | - | 0/5 | TOXIC 22% BWL |
|  | 93 (0-186) | 8 | 29.4 | 9.9 | 1.1 | 0/5 | HNTD ACTIVE |
|  | 322 (150-503) | 29 | 25.5 | 6.0 | 0.7 | 0/5 | MARGINAL ACTIVITY |
| CISPLATIN | - | - | - | - | - | 0/5 | TOXIC |
|  | - | - | - | - | - | 0/5 | TOXIC |
|  | 0 (0-0) | 0 | 48.1 | 28.6 | 3.3 | 1/5 | HNTD HIGHLY ACTIVE |
|  | 40 (0-179) | 4 | 30.8 | 11.3 | 1.3 | 0/5 | ACTIVE |
| CPT-11 CISPLATIN | - | - | - | - | - | 2/5 | TOXIC |
|  | - | - | - | - | - | 0/5 | TOXIC 28% BWL |
|  | 0 (0-0) | 0 | 53.7 | 34.2 | 4.0 | 0/5 | HNTD HIGHLY ACTIVE |
|  | - | - | - | - | - | 0/5 | TOXIC 28% BWL |
|  | 0 (0-0) | 0 | 43.7 | 24.2 | 2.8 | 0/5 | HIGHLY ACTIVE |
|  | 0 (0-0) | 0 | 39.8 | 20.3 | 2.4 | 0/5 | ACTIVE |
|  | 86 (0-211) | 8 | 29.2 | 9.7 | 1.1 | 0/5 | ACTIVE |
| CONTROL | 1119 (765-1818) |  | 19.5 |  |  | 0/10 |  |

TUMOR DOUBLING TIME = 2.6 DAYS. MICE AVERAGE WEIGHT: CPT-11 = 22.51 g, CISPLATIN = 24.26 g, COMBINATION = 23.30 g. ABBREVIATIONS USED: BWL = BODY WEIGHT LOSS, HNTD = HIGHEST NONTOXIC DOSE.

FIG. 1b

COMPOSITION COMPRISING CAMPTOTHECIN OR A CAMPTOTHECIN DERIVATIVE AND A PLATIN DERIVATIVE FOR THE TREATMENT OF CANCER

The present application claims the benefit of U.S. Provisional Application No. 60/190,055, filed Mar. 17, 2000; and of U.S. Provisional Application No. 60/193,398, filed Mar. 31, 2000.

The present invention relates to therapeutic associations for the treatment of cancer, comprising an effective amount of a camptothecin, or a camptothecin derivative, with an effective amount of an alkylating agent.

More specifically, the invention relates to anticancer treatments with associations of camptothecin derivatives such as irinotecan (CPT-11, CAMPTOSAR®), topotecan, 9-aminocamptothecin, 9-nitrocamptothecin, and alkylating agents, such as platinum coordination complexes, or platin derivatives. Such platin derivatives include cisplatin (cis-platinum, cis-diaminedichloroplatinum, or CDDP), carboplatin, and oxaliplatin.

European patent EP 137,145, specifically incorporated by reference herein, describes camptothecin derivatives of the formula:

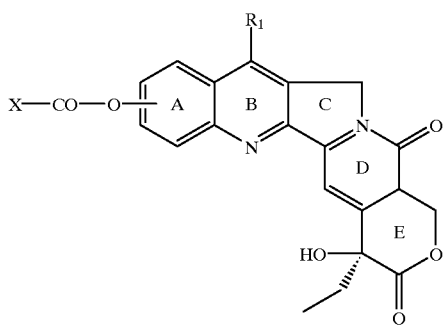

in which, in particular, $R_1$ is hydrogen, halogen or alkyl; X is a chlorine atom, or $NR_2R_3$, in which $R_2$ and $R_3$, which may be identical or different, may represent a hydrogen atom, an optionally substituted alkyl radical, a carbocycle or a heterocycle which are optionally substituted, or alkyl radicals (optionally substituted) forming, with the nitrogen atom to which they are attached, a heterocycle optionally containing another heteroatom chosen from O, S, and/or $NR_4$, wherein $R_4$ is a hydrogen atom or an alkyl radical; and in which the group X—CO—O— is located on ring A in position 9, 10, or 11.

These camptothecin derivatives are anticancer agents which inhibit topoisomerase I, among which irinotecan, in which X—CO—O— is [4-(1-piperidino-1-piperidino] carbonyloxy, is an active principle which is particularly effective in treatment of solid tumors. Camptothecin and camptothecin derivatives such as irinotecan are cytotoxic alkaloids which possesses strong anti-tumor activities. Irinotecan shows clinical activity against colon, gastric, ovarian, and small cell lung cancers, as well as non-Hodgkin's lymphoma (Bissery, M. et al., *Anti Cancer Drugs*, 7:166–174 (1996)).

The European patent application EP 74,256 also describes other camptothecin derivatives which are also mentioned as anticancer agents, in particular, derivatives of a structure analogous to the structure given above and in which X—CO—O— is replaced with a radical —X'R' for which X' is O or S, and R' is a hydrogen atom or an alkyl or acyl radical.

Other camptothecin derivatives have also been described, for example, in the following publications, patents, or patent applications: EP 56,692; EP 88,642; EP 296,612; EP 321, 122; EP 325,247; EP 540,099; EP 737,686; WO 90/03169; WO 96/37496; WO 96/38146; WO 96/38449; WO 97/00876; U.S. Pat. No. 7,104,894; JP 57 116,015; JP 57 116,074; JP 59 005,188; JP 60 019,790; JP 01 249,777; JP 01 246,287; and JP 91 12070; *Canc. Res.,* 38 (1997) Abstr. 1526 or 95 (San Diego, April 12–16); *Canc. Res.,* 55(3) :603–609 (1995); or *AFMC Int. Med. Chem. Symp.* (1997) Abstr. PB-55 (Seoul, Korea; July 27–August 1).

Camptothecin derivatives are usually administered by injection, more particularly intravenously in the form of a sterile solution or an emulsion. Camptothecin derivatives, however, can also be administered orally, in the form of solid or liquid compositions.

However, while camptothecin and camptothecin derivatives are considered as some of the most powerful substances possessing anti-tumor activity, the use of these compounds can be improved in clinical treatments by association with other antitumor agents.

Among such antitumor agents are platinum coordination complexes that possess antineoplastic activities. Platinum coordination complexes, or platin derivatives, include cisplatin (cis-platinum, cis-diaminedichloroplatinum, or CDDP), carboplatin, and oxaliplatin.

It has been discovered that the combination of a camptothecin such as irinotecan with cisplatin or oxaliplatin significantly reduces the development of tumor volume over what would be predicted from administration to tumor-infected mammals of each compound alone.

The combination of CPT-11 and cisplatin has been studied in Japan (Furuta, Tomio et al., *Cancer Chemotherapy,* 18(3): 393–402 (1991)). In that study, however, the evaluation of the combination was only conducted on L1210 mouse leukemia, and not on solid tumors. The route of administration of CPT-11 and cisplatin was via the abdominal cavity, that is, the drugs were administered intraperitoneally and not orally or intravenously. Furthermore, Furuta et al. did not evaluate the effect of the highest non-toxic dose of either CPT-11 or cisplatin as single agents. Without such a determination, the synergistic effect of the CPT-11 /cisplatin combination is impossible to evaluate.

It has now been found that the combination of CPT-11 and cisplatin is more active at a lower dose than the highest non-toxic dose of each single agent for the treatment of cancers, for example, in the treatment of colon adenocarcinoma.

It has also been found that the combination of CPT-11 and oxaliplatin is more active at a lower dose than the highest non-toxic dose of each single agent for the treatment of cancers.

The efficacy of a combination may be demonstrated by determination of therapeutic synergy. A combination manifests therapeutic synergy if it is therapeutically superior to one or the other of the constituents used at its optimum dose (T. H. Corbett et al., *Cancer Treatment Reports,* 66: 1187 (1982)).

The efficacy of a combination may also been demonstrated by comparison of the maximum tolerated dose of the combination with the maximum tolerated dose of each of the separate constituents in the study in question. This efficacy may be quantified, for example, by the $\log_{10}$ cell kill, which is determined by the following formula:

$$\log_{10} \text{ cell kill} = T\text{-}C(\text{days})/3.32 \times T_d$$

in which T-C represents the time taken for the cells to grow, which is the mean time in days for the tumors of the treated group (T) to reach a predetermined value (1 g for example) and the tumors of the control group (C) to reach the same value, and $T_d$ represents the time in days needed for the volume of the tumors in the control group to double (T. H. Corbett et al., *Cancer*, 40: 2660–2680 (1977); F. M. Schabel et al., *Cancer Drug Development*, Part B, *Methods in Cancer Research*, 17: 3-51, New York, Academic Press Inc. (1979)). An agent is considered to be active if $\log_{10}$ cell kill is greater than or equal to 0.7. An agent is considered to be very active if the $\log_{10}$ cell kill is greater than 2.8.

It has now been found that the combination of CPT-11 and oxaliplatin at 50% of the highest non-toxic dose for each agent achieved a better therapeutic response in the treatment of Glasgow osteosarcoma (GOS) than either agent administered alone, and is a known model system for osteosarcoma.

It has also been found that administration of CPT-11 in combination with cisplatin in the following manner with the following schedules results in a combination that is very highly active against colon adenocarcinoma. At certain dosage levels, the CPT-11 /cisplatin combination demonstrates synergistic activity against colon adenocarcinoma. Furthermore, the combination of CPT-11/cisplatin is more active at a lower dose than the highest non-toxic dose of either CPT-11 or cisplatin alone.

The products may be administered simultaneously, semi-simultaneously, separately, or spaced out over a period of time so as to obtain the maximum efficacy of the combination. As a result, the invention is not limited to the compositions obtained by the physical association of the drugs, but also includes those which permit separate administration, either simultaneously, semi-simultaneously, or spaced out over a period of time.

BRIEF DESCRIPTION OF THE DRAWING

FIG. 1 presents a table evaluating irinotecan (CPT-11), cisplatin, and the combination thereof as therapeutics against colon adenocarcinoma in a murine model system.

FIG. 1A presents data relating to Route, Dosage, Schedule, Total Dose, Fraction of Highest Non-Toxic Dose (HNTD), Drug Death, and Average Body Weight Change per Mouse at Nadir.

FIG. 1B presents data relating to Median Tumor Weight, T/C in %, Time for Median Tumor to Reach 1000 mg, T-C in days, Log Cell Kill, and Tumor Free Survivors.

EXAMPLE 1

The effect of the combination of CPT-11 and cisplatin was evaluated in a three-arm study in mice bearing colon adenocarcinoma C51. In the first arm, four dose levels of CPT-11 were given orally on days four through seven, twice daily. In the second arm, four dose levels of cisplatin were given intravenously on days four and seven. In the combination third arm, seven dosage levels of CPT-11 were administered orally on days four through seven, twice daily, with intravenous administration of seven dosage levels of cisplatin on days four and seven. This third arm illustrated an example of semi-simultaneous administration. The results obtained in the study of single agents CPT-11 and cisplatin and the combination CPT-11/cisplatin are given in Table I.

TABLE I

Evaluation of CPT-11 in Combination with Cisplatin Against Colon Adenocarcinoma C51 on BALB/c Female Mice CM-91

| Agent | Route | Dosage (mg/kg/adm) | Schedule (days) | $\text{Log}_{10}$ cell kill | T/C (days) | Time for Median tumor to reach 1000 mg in days | Comments |
|---|---|---|---|---|---|---|---|
| CPT-11 | p.o.; 0.2 ml | 132.2 | 4–7, twice/day | — | — | — | Toxic |
| CPT-11 | p.o.; 0.2 ml | 82.0 | 4–7, twice/day | — | — | — | Toxic |
| CPT-11 | p.o.; 0.2 ml | 50.8 | 4–7, twice/day | 1.1 | 9.9 | 29.4 | HNTD Active |
| CPT-11 | p.o.; 0.2 ml | 31.5 | 4–7, twice/day | 0.7 | 6.0 | 25.5 | Marginal Activity |
| Cisplatin | i.v.; 0.2 ml | 8.0 | 4, 7 | — | — | — | Toxic |
| Cisplatin | i.v.; 0.2 ml | 5.0 | 4, 7 | — | — | — | Toxic |
| Cisplatin | i.v.; 0.2 ml | 3.1 | 4, 7 | 3.3 | 28.6 | 48.1 | HNTD Highly Active |
| Cisplatin | i.v.; 0.2 ml | 1.9 | 4, 7 | 1.3 | 11.3 | 30.8 | Active |
| CPT-11 + Cisplatin | p.o.; 0.2 ml i.v.; 0.2 ml | 61.5 3.75 | 4–7, twice/day 4, 7 | — | — | — | Toxic |
| CPT-11 + Cisplatin | p.o.; 0.2 ml i.v.; 0.2 ml | 49.2 3.0 | 4–7, twice/day 4, 7 | — | — | — | Toxic |
| CPT-11 + Cisplatin | p.o.; 0.2 ml i.v.; 0.2 ml | 36.9 2.25 | 4–7, twice/day 4, 7 | 4.0 | 34.2 | 53.7 | HNTD Highly Active |
| CPT-11 + Cisplatin | p.o.; 0.2 ml i.v.; 0.2 ml | 24.6 3.0 | 4–7, twice/day 4, 7 | — | — | — | Toxic |
| CPT-11 + Cisplatin | p.o.; 0.2 ml i.v.; 0.2 ml | 49.2 1.5 | 4–7, twice/day 4, 7 | 2.8 | 24.2 | 43.7 | Highly Active |
| CPT-11 + | p.o.; 0.2 ml | 24.6 | 4–7, twice/day | 2.4 | 20.3 | 39.8 | Active |

TABLE I-continued

Evaluation of CPT-11 in Combination with Cisplatin Against Colon
Adenocarcinoma C51 on BALB/c Female Mice CM-91

| Agent | Route | Dosage (mg/kg/adm) | Schedule (days) | Log$_{10}$ cell kill | T/C (days) | Time for Median tumor to reach 1000 mg in days | Comments |
|---|---|---|---|---|---|---|---|
| Cisplatin | i.v.; 0.2 ml | 1.5 | 4, 7 | | | | |
| CPT-11 + | p.o.; 0.2 ml | 12.3 | 4–7, twice/day | 1.1 | 9.7 | 29.2 | Active |
| Cisplatin | i.v.; 0.2 ml | 0.75 | 4, 7 | | | | |

HNTD: Highest nontoxic dose;
p.o.: per os;
i.v.: intravenous;
T/C: Tumor growth delay
The data comprising this table was compiled from FIG. 1.

The combination of cisplatin and irinotecan was therapeutically superior to either of the single agents used at its optimum dose. Therefore, it can be seen that the CPT-11/cisplatin combination was synergistically active against colon adenocarcinoma at the highest non-toxic combination dose level, and highly active at other combination dose levels. Additionally, the combination showed greater therapeutic activity, in that the time for a median tumor to reach 1000 mg in days was longer at the highest non-toxic combination dose level than in either single agent administration of irinotecan or cisplatin at the highest non-toxic dose. Further, the irinotecan/cisplatin combination gave a broader dose response than the individual agents.

EXAMPLE 2

The effectiveness of irinotecan combination chemotherapy methods were tested in a dose response study in a murine tumor model. Three arms were evaluated for tolerance and efficacy. Tolerance was measured by mortality, body weight loss at nadir, host recovery time, and combination toxicity index. Efficacy end points for solid tumor models were tumor growth delay (T/C), log$_{10}$ cell kill (LCK, defined above), tumor regressions (i.e., complete remission (CR), or partial remission (PR)). For non-solid tumors, such as leukemia, efficacy was measured as the increase in life span (ILS).

Combination toxicity index (CTI) was calculated as the sum of the fraction of LD$_{10}$'s for each agent used in each combination (*Cancer Treatment Reports*, 66(5): 1187–1200 (1982)). The LD$_{10}$ for the single agent was obtained by plotting the toxicity of that agent and the dosage in mg/kg as a log probit graph. Subsequently, the CTI LD$_{10}$ was obtained by plotting as a log probit graph the observed lethality and the corresponding CTI calculated as the sum of the fraction of the LD$_{10}$ of each single agent. When the CTI equals one, only 50% of the LD$_{10}$'s of each agent can be used in combination without additional toxicity, and when the CTI equals two, 100% of the LD$_{10}$'s of each agent can be used in combination without additional toxicity.

The optimal total dose for oral and intravenous administration routes for irinotecan alone in various murine models is indicated in Table II.

TABLE II

Comparison of Oral and I.V. Irinotecan Administration

| Tumor (mice) | Route | Schedule days | Optimal Total Dose mg/kg | LCK |
|---|---|---|---|---|
| C51 | oral | 5, 7, 9, 13, 15, twice daily* | 845 | 2.5 |
| (BALB/c) | i.v. | 5, 7, 9, 13, 15, twice daily* | 615 | 3.0 |
| C26 | oral | 3–7 twice daily* | 558 | 0.9 |
| (BALB/c) | i.v. | twice daily* | 228 | 0.7 |
| P03 | oral | twice daily* | 900 | 3.4† |
| (B6D2F1) | i.v. | twice daily* | 346.2 | 3.2† |
| MA16/C | oral | 5–9 | 230.5 | 2.7 |
| (C3H/HeN) | i.v. | 5–9 | 130.5 | 2.6 |
| GOS | oral | 3–7 twice daily* | 900 | 2.1 |
| (B6D2F1) | i.v. | 3, 5, 7 twice daily* | 346.2 | 2.2 |

*The two administrations were 4 hours apart. †1/5 tumor free survivor on day 120.

Both methods of administration resulted in similar tolerance, as measured by body weight loss (8.5%), nadir (7 days post last administration), and recovery (5 days post nadir, i.e., 12 days post first administration). This study showed that the efficacy in tumor bearing mice was similar for oral and i.v. irinotecan administration across all five tumor models tested in three different mice strains. The oral maximum tolerated dose for irinotecan was shown to be about 1.4 to 2.6 times the i.v. maximum tolerated dose.

Cross-resistance was measured in murine leukemia cell lines. P388/CPT is a camptothecin-resistant leukemia that was established in vitro (*Biochem. Pharmacol.*, 45: 339 (1993) and maintained in vivo by i.p. passages in DBA2 female mice. The chemosensitivity of i.p. P388/CPT was evaluated with i.v. P388 sensitive reference drugs with different mechanisms of action. Antitumor efficacy was determined at the highest non-toxic dose as percent increase in life span (ILS), where:

$ILS = 100 \times [(\text{median day of death (MDD) of treated mice}) - (\text{MDD control mice})] \div (\text{MDD control mice})$ A minimal level of activity equals an ILS of greater than 26%. P388/CPT was found resistant to camptothecin s.c. and CPT-11, but sensitive to both cisplatin and oxaliplatin. These results show that this cell line was still sensitive to platin derivatives even when camptothecin resistance was present (Vrignaud, P. et al., *Proc. Amer. Assoc. Cancer Res.*, 35: 363, Abstract No. 2163 (1994)). Table III tabulates the results from this study.

TABLE III

| Agents\%ILS | P388 | P388/CPT (TFS) | Comment |
|---|---|---|---|
| CPT (sc) | 82 | 0 | resistant |
| CPT-11 (i.v.) | 91 | 0 | resistant |
| Cisplatin (i.v.) | 73 | 153 | sensitive |
| Oxaliplatin (i.v.) | 0 | 86 | sensitive |

The results for irinotecan (CPT-11) administered intravenously and simultaneously with representative alkylating agents are shown in Table IV.

TABLE IV

| CPT-11 plus: | Tumor site | Schedule | % HNTD of single agents | Host recovery (days) | Therapeutic response |
|---|---|---|---|---|---|
| cisplatin | C51 sc | simult. | 70 | 16 | = |
| oxaliplatin | GOS sc | simult. | 50 | 10 | ≧ |

HNTD represents the highest nontoxic dose. ≧: Better dose response for the combination. =: Equal dose response as each agent alone.

Table V compares different application methods for the agents alone and in combination, i.e., i.v. or per os (p.o.), as indicated.

TABLE V

| Agents | Tumor site | Schedule days | HNTD Dose mg/kg | LCK | CTJ | |
|---|---|---|---|---|---|---|
| CPT-11, i.v. | GOS, sc | 3, 5, 7 twice daily | 349.8 | — | 2.1 | |
| oxaliplatin, i.v. | | 3, 5, 7 | — | 10.2 | 2.3 | |
| combination | | | 226.8 | 10.8 | 2.3 | ≈0.94 |
| CPT-11, p.o. | GOS, sc | 4–8, twice daily | 806 | — | 2.5 | |
| oxaliplatin, i.v. | | 4–8 | — | 16.0 | 2.0 | |
| combination | | | 524 | 10.4 | 2.4 | ≈0.97 |
| CPT-11, p.o. | C51, sc | 4–7, twice daily | 406 | — | 1.1 | |
| cisplatin, i.v. | | 4, 7 | — | 6.2 | 3.3 | |
| combination | | | 295.2 | 4.5 | 4.0 | ≈1.4 |

HNTD represents the highest nontoxic dose.

This study confirmed the positive results obtained in Example 1. Irinotecan combined with oxaliplatin gave no antagonist activity, and was more effective than oxaliplatin alone against GOS (murine osteosarcoma model). Cisplatin and irinotecan in combination gave a very active therapeutic profile, and were more active than either agent alone. The CPT-11/cisplatin combination at its highest non toxic dose produced a $\log_{10}$ cell kill of 4.0, while the $\log_{10}$ cell kill of the highest non toxic dose of both CPT-11 and cisplatin as single agents were 1.1 and 3.3, respectively. Hence, this combination was therapeutic synergistic. The CPT-11/cisplatin combination was well tolerated, with a combination toxicity index of 1.4, indicating that 70% of the highest nontoxic does of the single agent could be combined without additional toxicity.

In conclusion, the combination of an alkylating agent, such as oxaliplatin or cisplatin, with irinotecan or other camptothecin derivative, is a highly active pharmaceutical composition and represents a new method for treating cancer.

I claim:

1. A method of treating a solid tumor in a mammal, said method comprising administering an effective amount of a synergistic therapeutic pharmaceutical composition, wherein said composition comprises an effective amount of at least two agents, wherein at least one agent is CPT-11 (irinotecan or 7-ethyl-10-[4-(1-piperidino)-1-piperidino]-carbonyloxy-camptothecin) and at least one agent is cisplatin, wherein said solid tumor is sensitive to said composition.

2. The method according to claim 1, wherein the at least two agents are administered simultaneously, semi-simultaneously, or separately.

3. The method according to claim 1, wherein said solid tumor is a colon adenocarcinoma.

4. The method according to claim 1, wherein said solid tumor is an osteosarcoma.

5. A method of treating a solid tumor in a mammal with a synergistic combination of CPT-11 (irinotecan or 7-ethyl-10-[4-(1-piperidino)-1-piperidino]-carbonyloxy-camptothecin) and a platin derivative, said method comprising administering orally an effective amount of CPT-11 as a first agent, and administering intravenously an effective amount of a platin derivative as a second agent, wherein said tumor is sensitive to said combination of CPT-11 and platin derivative.

6. The method according to claim 5, wherein the platin derivative is cisplatin.

7. The method according to claim 5, wherein the platin derivative is oxaliplatin.

8. The method according to one of claims 5, 6, or 7, wherein the agents are administered simultaneously, semi-simultaneously, or separately.

9. The method according to claim 5, wherein said solid tumor is a colon adenocarcinoma.

10. The method according to claim 5, wherein said solid tumor is an osteosarcoma.

11. A method of therapeutic administration of a synergistic anti-solid tumor composition to a mammal, said method comprising administering a combination of an effective amount of CPT-11 (irinotecan or 7-ethyl-10-[4-(1-piperidino)-1-piperidino]-carbonyloxy-camptothecin) and an effective amount of a platin derivative for the treatment of a solid tumor, wherein said solid tumor is sensitive to said combination, and wherein administration of the effective amounts is separate, simultaneous, semi-simultaneous, or is spaced out over a period of time.

12. The method according to claim 11, wherein the platin derivative is cisplatin.

13. The method according to claim 11, wherein the platin derivative is oxaliplatin.

14. The method according to claim 11, wherein said solid tumor is a colon adenocarcinoma.

15. The method according to claim 11, wherein said solid tumor is an osteosarcoma.

16. A therapeutic pharmaceutical composition comprising a synergistically effective combination of CPT-11 (irinotecan or 7-ethyl-10-[4-(1-piperidino)-1-piperidino]-carbonyloxy-camptothecin) and cisplatin, for the treatment of a solid tumor that is sensitive to said composition.

* * * * *